US005880811A

United States Patent [19]

Parisi

[11] Patent Number: 5,880,811

[45] Date of Patent: Mar. 9, 1999

[54] INFANT EYE TRAINER FOR A BABY BOTTLE

[76] Inventor: Richard Parisi, 2660 Harrison Ave., Oceanside, N.Y. 11572

[21] Appl. No.: 856,467

[22] Filed: May 14, 1997

Related U.S. Application Data

[63] Continuation-in-part of Ser. No. 578,462, Dec. 26, 1995, abandoned.

[51] Int. Cl.[6] .......... A61B 3/00

[52] U.S. Cl. .......... 351/203; 351/246; 248/106

[58] Field of Search .......... 351/203, 200, 351/246; 248/102, 103, 104, 105, 106, 107

[56] References Cited

U.S. PATENT DOCUMENTS

| | | |
|---|---|---|
| 3,729,199 | 4/1973 | Granberg . |
| 4,295,293 | 10/1981 | Baclit . |
| 4,320,883 | 3/1982 | Bass . |
| 5,072,843 | 12/1991 | James . |
| 5,083,732 | 1/1992 | Akamine . |
| 5,129,610 | 7/1992 | Campbell . |
| 5,664,746 | 9/1997 | Benzakarya .......... 248/106 |

OTHER PUBLICATIONS

Complete baby and child care, p. 12, by Dr. Miriam Stoppard, 1995.

The Well Baby, pp. 148 and 149 by Michael Samuels M.D., 1991 Stage I: Birth to 1 Month, p. 83.

Compton's Interactive Encyclopedia, 1994–1995.

*Primary Examiner*—Hung Xuan Dang
*Attorney, Agent, or Firm*—Michael I. Kroll

[57] ABSTRACT

An infant eye trainer (10) for a baby bottle (12) comprising a structure (14) for gripping the baby bottle (12). An extension member (16) extends from the gripping structure (14). A visually attractive ornament (18) on a distal free end of the extension member (16), will help keep the eyes (20) of an infant (22) focused in a straight manner towards the ornament (18), thereby preventing the eyes (20) of the infant (22) from crossing when the infant (22) is nursing with the baby bottle (12).

6 Claims, 4 Drawing Sheets

| | | | |
|---|---|---|---|
| 46 | 'A' (INCHES) | 'B' (BOTTLE SIZE - OZ) | 44 |
| 50 | 8 1/2 | 4 | 48 |
| 54 | 12 | 8 | 52 |

INFANT EYE TRAINER FOR A BABY BOTTLE

CROSS-REFERENCE TO RELATED APPLICATION

This application is a continuation-in-part of my U.S. patent application Ser. No. 08/578,462, filed 26 Dec. 1995, entitled "Infant Eye Trainer for a Baby Bottle," now abandoned.

BACKGROUND OF THE INVENTION

1. Field of the Invention

The instant invention relates generally to baby bottle holders and more specifically it relates to infant eye trainers and visually stimulating devices for a baby bottle.

Studies have shown that the most crucial developmental months for an infant is from birth to about six months. Muscles and senses are developing rapidly, and during that period, you want to make sure they are developing correctly. That is why it is important to keep the infant's eyes straight, while feeding them from a baby bottle. Often, most infants have nothing to focus their eyes on, so they look at the bottle. By doing this, both eyes naturally cross, due to the position the bottle is in. If the infant does this often enough, in those precious developing stages, there is a possibility that one or both eyes can be slightly off centered permanently.

2. Description of the Prior Art

Numerous baby bottle holders have been provided in the art. For example, U.S. Pat. Nos. 4,295,293 (Baclit), 4,320,883 (Bass), 5,083,732 (Akamine) and 5,129,610 (Campbell) all are illustrative of such art. While these devices may be suitable for the particular purpose to which they address, they would not be as suitable for the purposes of the present invention as heretofore described.

U.S. Pat. No. 4,295,293 (Baclit, Paul S.), entitled "Nursing Bottle Holder," discloses a baby bottle holder including a main support member in the form of a shell which fits over the body of the infant when the infant is lying down. An upright bottle support removably mounted on the main support for mounting the bottle. This bottle support has a caricature thereon such as of an animal. A bottle carriage on the bottle support is pivoted between an active position in which an infant feeds, and an inactive position in which it is inclined away from the infant's face, and has a weight for moving it to an inactive position when the bottle is released. The bottle support includes a music box which is activated by the bottle carriage when the latter is moved to an inactive position. The main support while carrying the bottle support is demountably positionable on a pull-toy, such as a buggy which, together as a combination toy can be enjoyed by an older child.

U.S. Pat. No. 4,320,883 (Bass, Wayne E.), entitled "Positional Toy/Bottle Holder," discloses a positionable support for a baby bottle comprising interchangeable head members with openings representing the mouth of the characterization which the head represents. The opening contains a groove or channel for receiving and holding a resilient ring member which grasps and firmly holds a baby bottle. An extension arm supports the head member at a distance spaced from the base member. The extension arm, head and base member attachments are pivotable. The head member is removable from the extension arm pivot connection. A novel valve is included to prevent liquid from flowing from the nipple attached end of the baby bottle from the effect of gravity on the liquid therein.

U.S. Pat. No. 5,083,732 (Akamine, Horace S.), entitled "Flexible Baby Bottle Holding Animal," discloses an improved baby bottle holder, specifically for use in feeding and storing the baby's food and to facilitate the easy reach by the baby and for other functions. A single-piece flexible holding device has four major components, namely a multi-use clamp, a protective sheath cover which provides a protection for safe use, beauty, and is designed to bend with the movements of a flexible rod. This flexible rod is adopted from those in common desk lamps. Finally a flexible holding grip that can hold a bottle placed within it by flexibly spreading itself open upon insertion of the bottle and will hold bottles of a variety of widths. The grip has a parallel gap which allows it to adapt to various bottle designs. The device is advantageously built into an animal, such as a toy bear, with the grip and clamp in place of the bear's hands.

U.S. Pat. No. 5,129,610 (Campbell, Gregory A.), entitled "Gimballed Adjustable Holder for Nursing Bottle," discloses a gimballed adjustable holder for a nursing bottle comprised of a base assembly, a gimbal support which is vertically adjustable with respect to the base assembly and rotatable about the base and gimbal support pivot for use in various positions and locations, an inner gimbal and outer gimbal, which permits pivotal movement of the nursing bottle in order to compensate for movements of an infant during feeding. The bottle is held in place within the inner gimbal in a bottle support and secured via a bottle retention strap.

BRIEF SUMMARY OF THE INVENTION

A primary object of the present invention is to provide an infant eye trainer for a baby bottle that will overcome the shortcomings of the prior art devices.

Another object is to provide an infant eye trainer for a baby bottle that will help keep the eyes of the infant focused in a straight manner, thereby to prevent the eyes of the infant from crossing while bottle feeding.

An additional object is to provide an infant eye trainer for a baby bottle that will also help the infant to build concentration when looking at a face of a head on an elongated neck extending from the baby bottle.

A further object is to provide an infant eye trainer for a baby bottle that is simple and easy to use.

A still further object is to provide an infant eye trainer for a baby bottle that is economical in cost to manufacture.

Another object is to provide an infant attracting device for a baby bottle that will provide visual stimulus to the infant while nursing.

Further objects of the invention will appear as the description proceeds.

The foregoing and other objects, advantages and characterizing features will become apparent from the following description of certain illustrative embodiments of the invention.

The novel features which are considered characteristic for the invention are set forth in the appended claims. The invention itself, however, both as to its construction and its method of operation, together with additional objects and advantages thereof, will be best understood from the following description of the specific embodiments when read and understood in connection with the accompanying drawings. Attention is called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views.

DETAILED DESCRIPTION OF THE PREFERRED EMBODIMENTS

Figure 1:
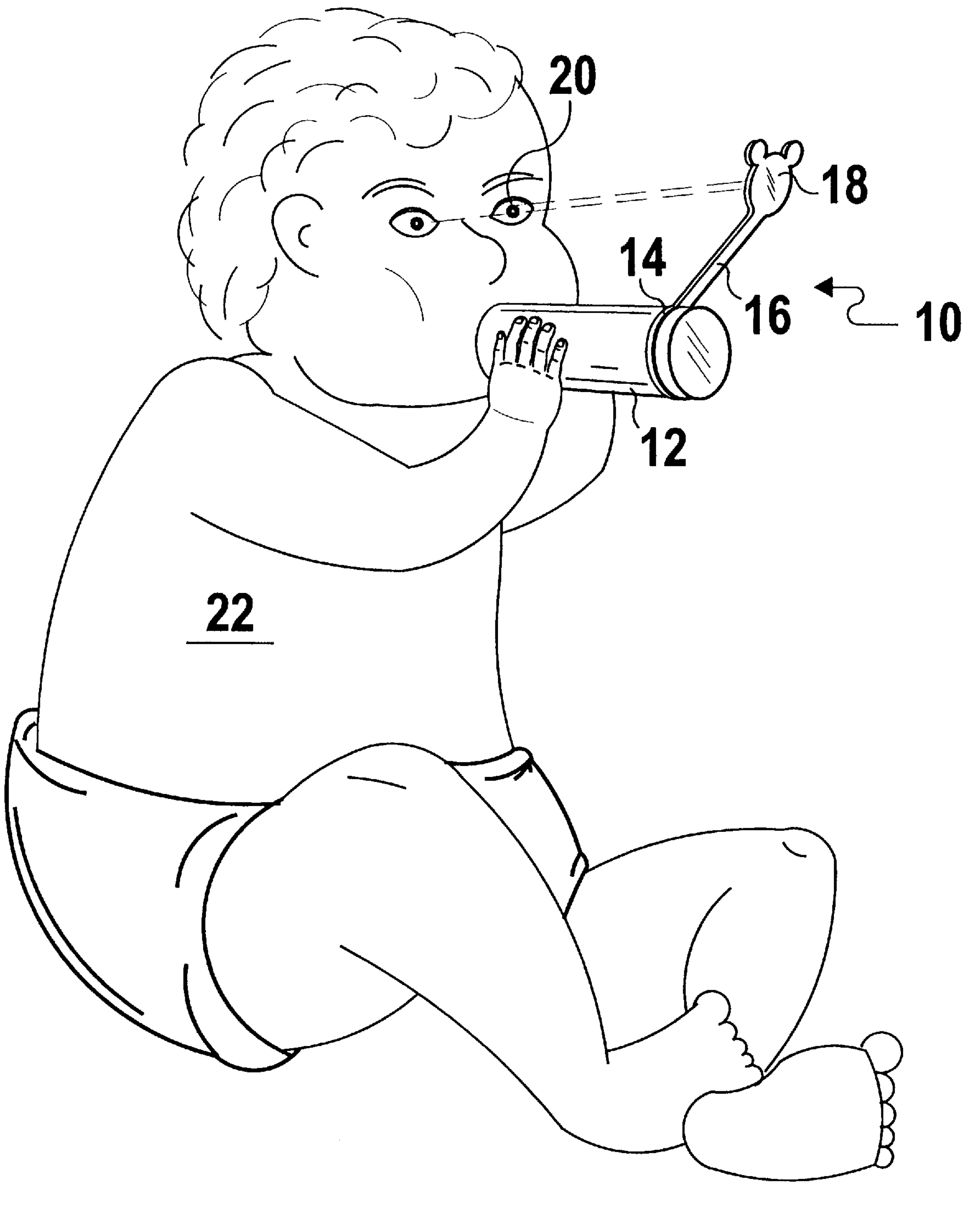
FIG. 1 is a perspective view showing the instant invention in use when an infant is feeding with a baby bottle.

Turning now descriptively to the drawings, in which similar reference characters denote similar elements throughout the several views, the Figures illustrate the infant eye trainer for a baby bottle of the present invention. With regard to the reference numerals used, the following numbering is used throughout the various drawing figures.

Figure 2:
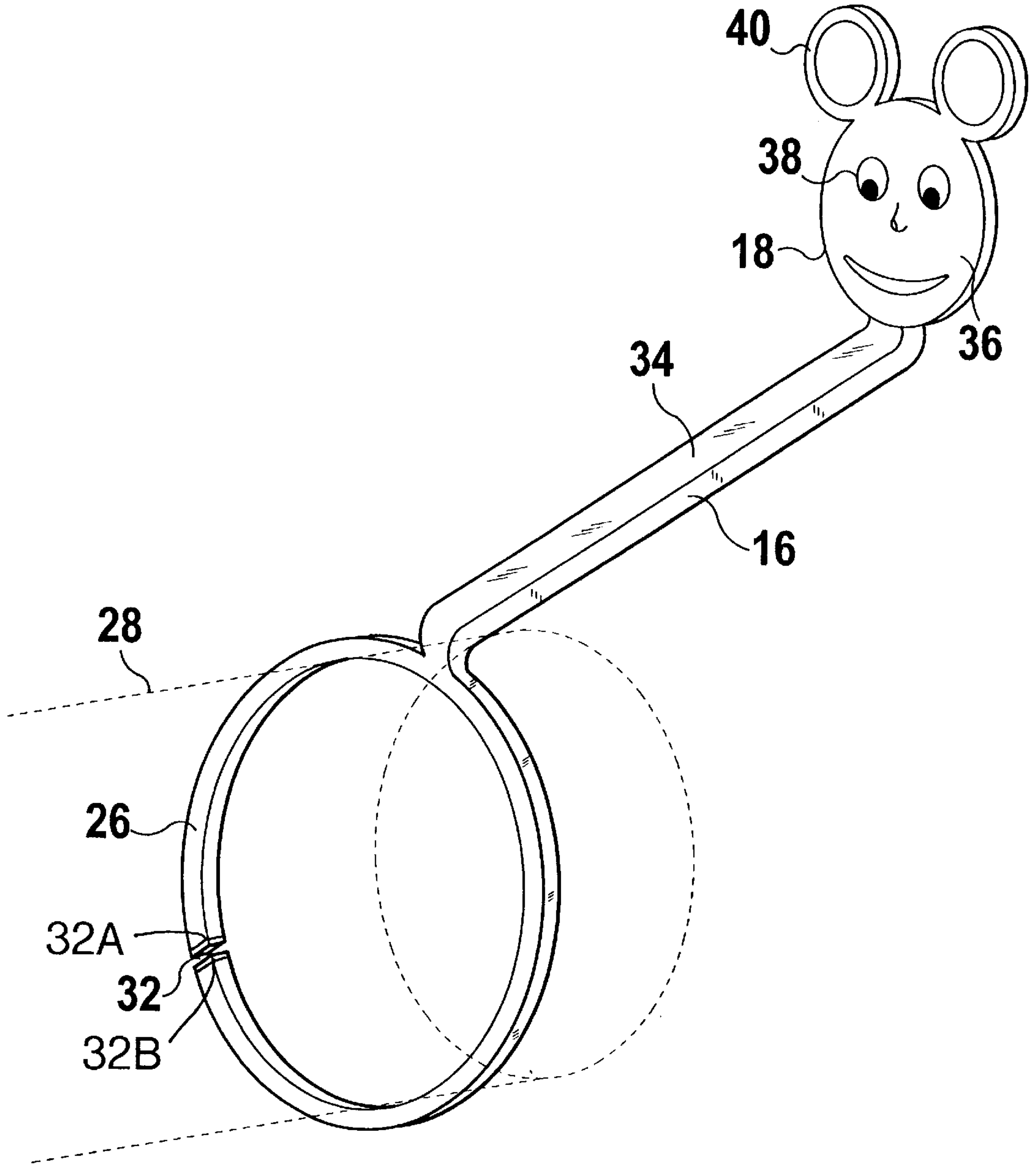
FIG. 2 is a an enlarged front perspective view of the instant invention.
Figures 3, 4:
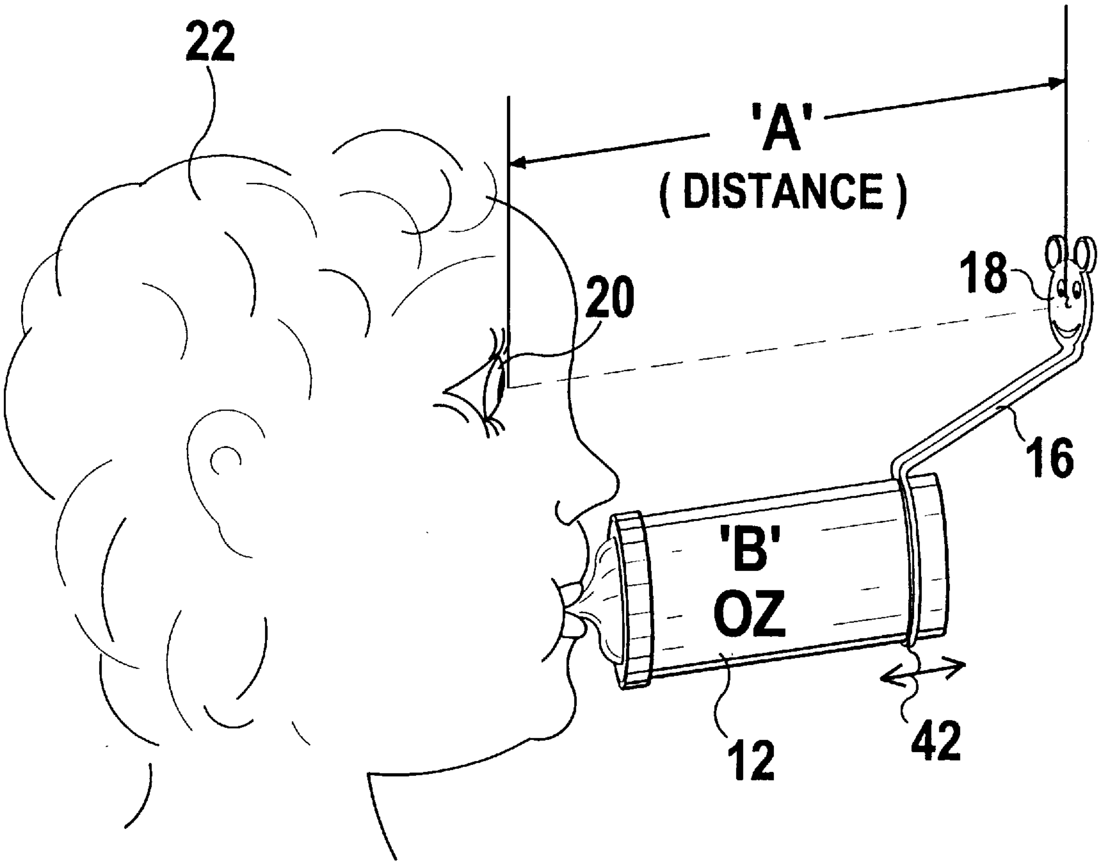
FIG. 3 is a chart illustrating the approximate focal length between the infant's eyes and the viewable member on the instant invention, and how it varies with the size of the bottle used.
FIG. 4 is a side perspective view of an infant feeding with a standard 4 ounce baby bottle utilizing the instant invention.
Figure 5:
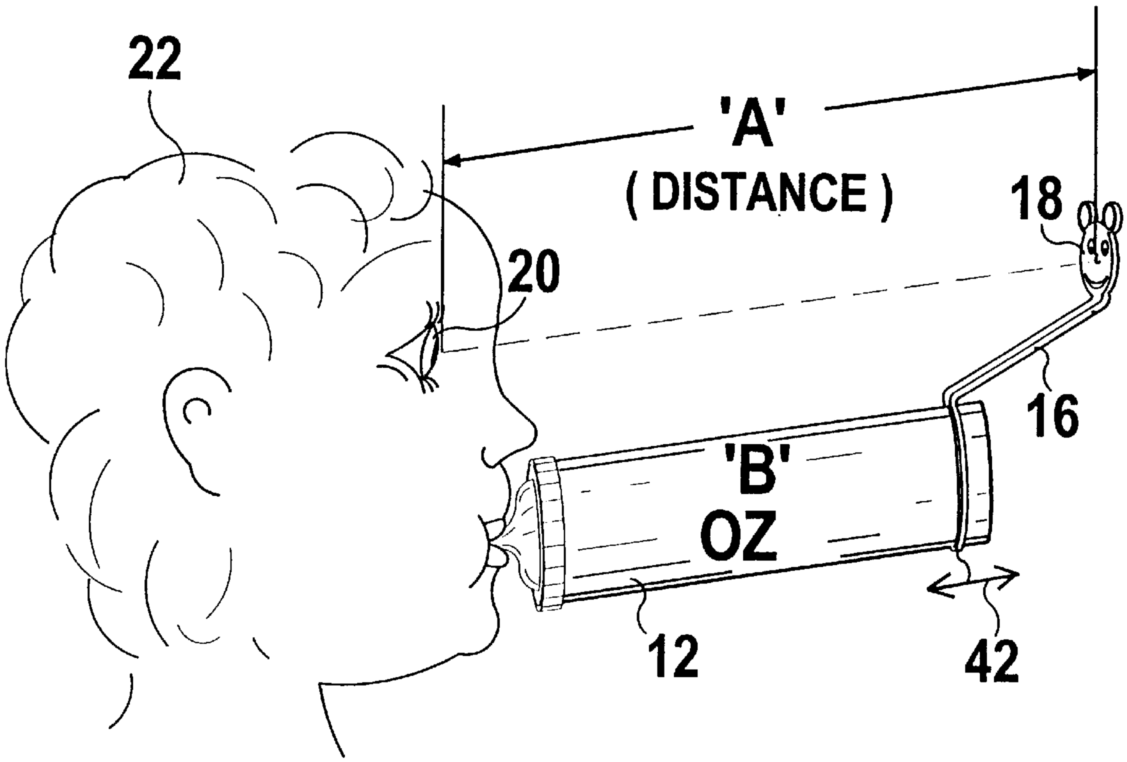
FIG. 5 is a side perspective view of an infant feeding with a standard 8 ounce baby bottle utilizing the instant invention.

FIGS. 1 through 5 illustrate an infant eye trainer/attracting device 10 for a baby bottle 12 comprising a structure 14 for gripping the baby bottle 12. An extension member 16 extends from the gripping structure 14. An ornament 18 on a distal free end of the extension member 16, will help keep the eyes 20 of an infant 22 focused in a straight manner towards the ornament 18, thereby preventing the eyes 20 of the infant 22 from crossing while nursing with the baby bottle 12.

The gripping structure 14 is preferably a flexible split clamp ring 26 that fits about a body portion 28 of the baby bottle 12. The flexible split clamp ring 26 can include mating hook and loop pile fastener material in the split portion 32 thereof, so as to hold the flexible split clamp ring 26 securely to the body portion 28 of the baby bottle 12. When utilizing hook and loop pile fastener material in the split portion, it is preferred that the clamp ring be split at an angle such that the exposed ends of the clamp ring overlap each other with facing and overlapping surfaces, the facing surfaces having mating hook and loop piles 32*a* and 32*b* respectively to hold the clamp ring securely to the body portion of the bottle.

The extension member 16 is preferably an elongated flat neck 34. The extension member 16 serves to orient the ornament 18 directly in front of the infant's eyes 20 at an appropriate distance.

It is generally agreed that newborns and infants can focus best at distances from about 6 to about 12 inches from the eye, preferably from about 7 to about 10 inches. For example, Compton's Interactive Encyclopedia (Compton's NewMedia, Inc., 1994, 1995) states that newborn babies focus most easily at a distance of about 10 inches. In *The Well Baby* (Mike Samuels, M.D., 1991) it is stated that the "newborn focuses best at a distance of 7½ inches." In *Complete Baby and Child Care* (Dr. Miriam Stoppard, 1995), it is stated that a newborn "baby can see clearly up to a distance of 8–10 inches". Accordingly, it is preferred that the ornament should be oriented this far from the eyes of the infant.

A standard 8 ounce baby bottle is about 8 inches long. With these bottles, the extension member can extend straight up from the gripping member (perpendicular to the longitudinal axis of the bottle). As long as the gripping member is placed within the bottom two inches of the bottle, the ornament will be maintained at an appropriate distance for viewing by the infant, about 6 to 8 inches. Alternatively, the extension member for these bottles can extend up to about 2 inches past said gripping means, measured along an axis parallel to the longitudinal axis of the bottle, so that the gripping means can be placed anywhere along the bottom half (4 inches) of the bottle.

A standard 4 ounce baby bottle, however, is only about 4 inches long. With these bottles, the extension member must necessarily extend at least about 2 inches past said gripping means, measured along an axis parallel to the longitudinal axis of the bottle, so that the ornament is at least 6 inches from the infant's eyes. An extension of between about 2 and about 5 inches allows the invention to be utilized with virtually all baby bottles from about 4 to about 8 inches in length, while maintaining a proper focal distance from the infant, about 6 to about 12 inches. For general use, an extension of from about 3 to about 4 inches is preferable. It can be readily appreciated that by sliding 42 the gripping means 14 along the bottle 12, the user can easily adjust the orientation of the ornament 18 to an appropriate distance from the eyes 20 of the infant 22.

The ornament 18 is visually stimulating and is preferably a flat head 36. It is well known that newborns and infants prefer to look at generally round shapes with clear edges, such as, for example, faces, nipples or targets. Accordingly, the ornament should be generally round with clear edges. For example, a cartoon type face 38 can be placed upon the flat head 36. The ornament 18 can further include a pair of loop ears 40 on a top portion of the flat head 36.

In its preferred form, the gripping structure 14, the extension member 16 and the ornament 18 are integral and fabricated out of the same kind of material 42. The material 42 is preferably either plastic or rubber.

The infant eye trainer 10 for a baby bottle 12 optionally includes a spring portion, to make the elongated flat neck 34 more flexible. This causes the ornament 18 to move back and forth to attract the attention of the eyes 20 of the infant 22 thereto.

To use the infant eye trainer 10, the following steps should be taken.

1. Open the split portion 32 of the flexible split clamp ring 26.

2. Slip the flexible split clamp ring 26 over the body portion 28 of the baby bottle 12, with the cartoon type face 38 on the flat head 36 facing the nipple on the baby bottle 12.

3. Move the flexible split clamp ring 26 along the length of the body portion 28 of the baby bottle 12 to a proper position, i.e. so that the ornament 18 is from about 6 to about 12 inches from the eye 20 of the infant 22.

4. Allow the infant 22 to feed with the baby bottle 12 oriented so that the ornament 18 is directly in from of the eyes 20 of the infant 22 so the infant 22 can focus directly on the cartoon type face 38.

It will be understood that each of the elements described above, or two or more together, may also find a useful application in other types of applications differing from the type described above. For example, the instant invention may find utility as a simple infant attracting device for providing visual stimulus to the infant.

While the invention has been illustrated and described as embodied in an infant eye trainer for a baby bottle, it is not intended to be limited to the details shown, since it will be understood that various omissions, modifications, substitutions and changes in the forms and details of the formulation illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of this invention.

What is claimed as new and desired to be protected by Letters Patent is set forth in the appended claims:

1. An infant eye trainer for a baby bottle supported by said baby bottle comprising:

a) means for gripping the baby bottle comprising a flexible split clamp ring fitted about a body portion of the baby bottle, said ring being split at an angle such that the exposed ends overlap each other, said exposed ends having mating hook and loop pile fastener for holding said ring securely on said baby bottle;

b) an elongated flat neck extension member extending from said gripping means; and c) a visually stimulating ornament having a flat head shape generally round in shape with clear edges on a distal free end of said extension member, said ornament being positioned about 7 to about 10 inches from the eyes of said baby, said gripping means, extension member and ornament being integral and fabricated out of the same kind of material.

2. An infant eye trainer for a baby bottle as recited in claim 1, wherein said ornament includes a cartoon type face placed upon said flat head.

3. An infant eye trainer for a baby bottle as recited in claim 2, wherein said ornament further includes a pair of loop ears on a top portion of said flat head.

4. An infant eye trainer for a baby bottle as recited in claim 1, wherein said material is plastic.

5. An infant eye trainer for a baby bottle as recited in claim 1, wherein said material is rubber.

6. The method of training the eyes of an infant to help keep the eyes of the infant focused in a straight manner to prevent the eyes of the infant from crossing during bottle feeding comprising the steps of:

a) placing on said bottle a flexible split clamp ring split at an angle such that the exposed ends overlap each other, said exposed ends having mating hook and loop pile fastener for holding said ring securely on said baby bottle, an elongated flat neck extension member extending from said gripping means, and a visually stimulating ornament having a flat head shape generally round in shape with clear edges on a distal free end of said extension member, said gripping means, extension member and ornament being integral and fabricated out of the same kind of material; and b) positioning said split ring on said baby bottle so that said ornament is about 7 to about 10 inches from the eyes of said baby.

* * * * *